United States Patent [19]

N'Guyen

[11] 4,204,768
[45] May 27, 1980

[54] GAS ANALYSERS OF THE SELECTIVE RADIATION ABSORPTION TYPE WITH A CALIBRATION CELL

[75] Inventor: Van L. N'Guyen, Paris, France

[73] Assignee: Sereg, Montrouge, France

[21] Appl. No.: 916,395

[22] Filed: Jun. 16, 1978

[30] Foreign Application Priority Data

Jun. 21, 1977 [FR] France ................... 77 18904

[51] Int. Cl.² .......................... G01J 1/02; G01N 21/00
[52] U.S. Cl. ..................................... 356/243; 356/439; 250/343
[58] Field of Search ................ 356/51, 243, 439; 250/343, 344, 252

[56] References Cited

U.S. PATENT DOCUMENTS

| 3,562,522 | 2/1971 | Cederstrand et al. | 250/252 |
| 3,728,540 | 4/1973 | Todd et al. | 356/51 |
| 3,898,462 | 8/1975 | Ishida et al. | 250/344 |
| 3,980,517 | 9/1976 | MacTaggart | 356/243 |

Primary Examiner—Vincent P. McGraw

Attorney, Agent, or Firm—W. R. Sherman; Kevin McMahon

[57] ABSTRACT

A gas analyser of the infra-red radiation absorption type, particularly for measuring the amounts of $CO_2$ and CO in vehicle exhaust gases, comprises a pair of infra-red radiation sources arranged to direct their radiation along a measurement path and a reference path respectively, the radiation entering each path being periodically interrupted by a rotating commutator. Two measurement chambers for receiving the gas to be analysed and respective detection chambers for $CO_2$ and CO are alternately disposed along the measurement path, while two reference chambers and two more such detection chambers are alternately disposed along the reference path, corresponding detection chambers being connected to respective differential pressure sensors of the variable capacitance type. The analyser includes a calibration cell containing predetermined concentrations of $CO_2$ and CO. The cell is selectively interposable in the measurement path, and is connected to a flexible-wall chamber. The flexible-wall chamber defines with the cell a sealed enclosure, and serves to maintain the pressure within the sealed enclosure equal to ambient pressure.

5 Claims, 1 Drawing Figure

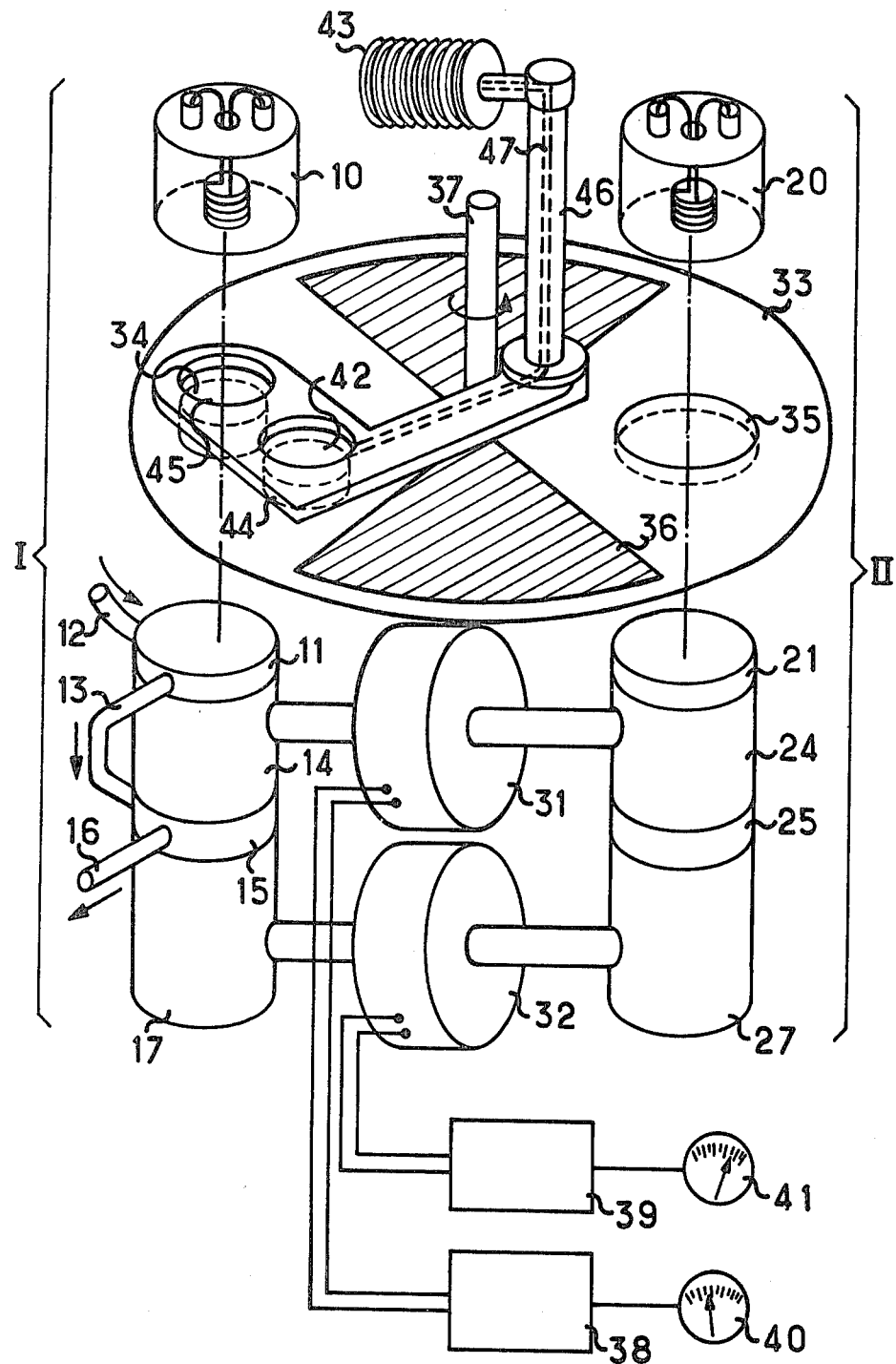

GAS ANALYSERS OF THE SELECTIVE RADIATION ABSORPTION TYPE WITH A CALIBRATION CELL

The present invention relates to gas analysers of the selective radiation absorption type, such as those using infra-red radiation, and is more particularly concerned with improvements in calibration devices for such apparatus for compensating the influence of variations of pressure and temperature on their indications.

It is known that analysers of the infra-red type generally comprise a source of radiation, an optical commutator for periodically directing the radiation along a measurement path and along a reference path, and a measurement detector constituted by a cell sensitive to differential pressure variations and comprising a variable condenser microphone of which the separation of the electrodes is modulated, at the frequency of the commutator, as a function of the pressure differences to which it is subjected. The voltage thus obtained at the output of the detector is, after amplification, demodulation and filtering, representative of the amount of gas to be measured, which amount is displayed on an indicator.

This type of apparatus requires periodic recalibration in consequence of the drift with time in parameters of its various components, such as the source and the detector, and the inevitable presence of dirt on the optical paths, etc.

The problem of recalibration is easily resolved in the laboratory by means of bottles of calibration gas: a bottle of neutral gas, for example nitrogen, permits the zero of the indicator of the apparatus to be adjusted by filling the measurement container with this neutral gas, and a bottle of the gas whose amount is to be measured permits the scale adjustment to be made by introducing a mixture of given concentration of this gas whose amount is to be measured in the measurement container and by adjusting the gain of the amplifier in order that the indicator displays this given concentration.

However, these calibration operations by means of bottles of calibration gas are delicate and hardly practicable for carrying out by non-specialised personnel, as is the case for example for motor mechanics responsible for checking the amounts of the oxides CO and $CO_2$ in the exhaust gas of vehicles, during the adjustment of their carburators in order to meet regulations for limiting pollution in this domain.

The method of calibration thus consists in practice of utilising air as the neutral gas for the zero adjustment, and of replacing the gas of known concentration supplied from a bottle for the scale adjustment by a shutter or a metallic grill which simulates only very crudely the phenomenon of selective absorption.

To the errors due to this imperfect method of calibration are added other causes of error, resulting from variations of pressure and temperature of the gas to be measured, for the number of molecules of this gas which are contained in the measurement chamber (which is of fixed dimensions) and influencing the transmission of the radiation towards the detector, is obviously a function of these physical parameters. The following observations have been made.

(a) At constant pressure, the effect of variations of temperature on the gas introduces a measurement error of about $\pm 6.5\%$ (while the tolerance fixed by the standards is $\pm 2.7\%$): this requires a compensation of the effect of temperature, or a thermostatic control bringing the gas to be measured to a reference temperature.

(b) At constant temperature, the effect of the variation of atmospheric pressure can be even more important. In a given place, extreme variations of atmospheric pressure of $\pm 50$ millibars result in an error of about $\pm 5\%$ (hence the necessity of regulating the pressure of the gas to be measured in certain cases). Similarly, the indication of the apparatus as a function of the altitude of the place of use can also vary by significant amounts. For example, between sea level and 2000 meters in altitude, which corresponds to a pressure variation of 220 millibars, the value displayed on the indicator can be in error by 22% in the case of the amount of CO and $CO_2$.

To overcome these errors, apparatus in accordance with preferred embodiments of the invention is provided with novel means for calibration, which take account of external conditions of pressure and temperature, whatever they are.

According to the present invention, a gas analyser of the selective radiation absorption comprises: at least one source of radiation;

a measurement chamber for receiving a gaseous mixture containing at least one gas whose concentration is to be measured, said measurement chamber being disposed in a measurement path to receive radiation from the source;

means for periodically interrupting the radiation entering said measurement path;

at least one detector sensitive to, and disposed to receive, radiation which has passed through the measurement chamber; and a calibration cell for cooperating with the said path, said cell enclosing a given concentration of the gas whose concentration is to be measured in a sealed enclosure.

Thanks to this arrangement, the influence of pressure can be taken into account during the calibration of the apparatus, since the calibration cell, by its construction, can readily be arranged to take the same pressure as the ambient atmospheric pressure. As far as temperature is concerned, its influence can be neutralised in several ways: for example by bringing the gas to be analysed to a substantially constant temperature at which the calibration cell is maintained, or by leaving the calibration cell at ambient temperature during the calibration, and by bringing the gas to be analysed, under the normal operating conditions of the apparatus, to this temperature. The second solution, which appears more simple, can easily be put into practice by making the gas to be analysed follow a sufficiently long path to have time to cool to, or to reach, ambient temperature.

A particular embodiment of the invention, applied to measuring the amount of gases $CO_2$ and CO present in the exhaust gases of vehicles, will now be described, by way of non-limiting example only, with reference to the attached drawing, which is a somewhat schematic representation of an analyser according to the invention in perspective view. However, it is to be understood that the invention is not limited to this sole embodiment, and that it can be applied to measuring the amount of a single gas other than CO or $CO_2$.

The analyser shown in the drawing comprises a measurement path I and a reference path II. The path I comprises an infra-red radiation source 10 and successively in the path of radiation, a measurement chamber 11 for $CO_2$ provided with inlet and outlet pipes 12 and 13 for the gases to be analysed, a detector 14 for $CO_2$, a second measurement chamber 15 for CO, also provided with inlet and outlet pipes 13 and 16, and a detector 17 for CO.

Symmetrically, the reference path II comprises analogous elements: a source 20, a reference chamber 21, a detector 24 for $CO_2$, a second reference chamber 25 and a detector 27 for CO. The reference chambers 21 and 25, of the same thickness as the chambers 11 and 15, are filled with a gas neutral to the radiation, such as nitrogen. The detectors 14 and 24 for $CO_2$ are two chambers filled with $CO_2$ and respectively communicating with the two halves of a chamber 31 constituting a well known device sensitive to variations of differential pressure. The two halves of the chamber 31 are separated by a flexible membrane forming one of the electrodes of a variable condenser, the second electrode being fixed, so that pressure differences applied to the membrane are converted into corresponding electrical signals. Similarly, the detectors 17 and 27 for CO are two chambers filled with CO and communicating with the two halves of another chamber 32 analogous to the chamber 31.

The analyser also includes an optical modulator comprising a fixed disc 33 having two apertures 34, 35 aligned with the sources 10, 20 respectively, and a rotor 36 in the shape of a double fan driven to rotate around an axis of symmetry 37 by an electric motor (not shown), for example at a speed of the order of 1500 turns a minute. This modulator is interposed between the sources 10, 20 and the chambers 11, 21 and it permits the respective radiation of these sources to be periodically interrupted on the paths I and II, for example at the frequency of 50 Hz.

The electrodes of the condensers of the chambers 31 and 32 are respectively connected to the inputs of two electronic processing chains 38, 39 in order to amplify, demodulate and filter the measurement signals produced thereby and to display the results on the $CO_2$ indicator 40 and the CO indicator 41.

According to the invention, the analyser further comprises a calibration cell 42, filled with the gas to be measured in known proportions. The cell 42 is constituted by a circular chamber closed at its ends by two windows of material transparent to the radiation, for example of fluoride, which are mounted parallel to each other in planes perpendicular to the direction of the radiation. The cell 42 is in communication with a flexible-wall enclosure 43, such as for example a bellows, and as a result, the calibration gas enclosed in the cell 42 can expand freely as a function of ambient temperature and pressure. In the example shown, the cell 42 is mounted on an arm 44 which also carries a fluoride disc 45 of thickness equivalent to that of the two windows closing the cell 42, and this arm 44 can pivot around the axis of a shaft 46, under manual or electric control, and thus take two positions: a first, or calibration, position in which the cell 42 is interposed in one of the two optical paths, preferably the measurement path I; and a second, or measurement, position in which the disc 45 is substituted in place of the cell 42 in the same optical path to restore the attenuation provided by the fluoride windows of the cell 42. The enclosure 43 is for example mounted on the shaft 46 and is connected to the cell 42 by an internal conduit 47 provided in the shaft 46 and the arm 44. In order that the two optical paths are balanced, an equivalent thickness of fluoride is also interposed in the orifice 35 on the reference path II. A calibration operation is effected in the following manner.

(a) Zero adjustment. Assuming that the two paths I and II are optically balanced, the measurement chambers 11 and 15 are filled with neutral gas, or in the absence of this with pure air with negligible amounts of $CO_2$ and CO, and the zero adjustment of the two indicators 40 and 41, for $CO_2$ and CO respectively, is effected in the usual manner. The arm 44 is in this case in the measurement position (as shown in the drawing) in order to present in the optical path I the same thickness of fluoride as in the reference path II.

(b) Scale adjustment. Assuming for example that in the analyser of CO and $CO_2$ under consideration, the measurement chambers 11 and 15 for $CO_2$ and CO have thicknesses of 1 millimeter and 5 millimeters in the optical path of the radiation respectively, and that it is desired to adjust the two scale points representing 10.5% of $CO_2$ and 4.5% of CO, the calibration cell is filled with a mixture of calibration gas containing 10.5% of $CO_2$, 27% of CO (since the radiation must traverse 6 millimeters of chamber before reaching the CO detector 17 in normal operation), and the remainder nitrogen or another neutral gas. The measurement chambers 11 and 15 are filled with neutral gas, or in the absence of this with pure air, the arm 44 is placed in the calibration position, so as to interpose the cell 42 in the optical path I. The respective gains of the amplifiers of the channels 38 and 39 are then adjusted in order to display on the indicators 40 and 41 10.5% of $CO_2$ and 4.5% of CO respectively.

The calibration thus effected takes account both of the pressure and temperature to which the analyser, and more precisely the enclosure 43 (whose volume can be larger than that of the cell 42), is subject. Its position in the path of the gases to be analysed can also be chosen to assure a better equilibrium of temperatures during the calibration.

What is claimed is:

1. A gas analyser of the selective radiation absorption type, comprising:

at least one source of radiation;

a measurement chamber for receiving a gaseous mixture containing at least one gas whose concentration is to be measured, said measurement chamber being disposed in a measurement path to receive radiation from the source;

means for periodically interrupting the radiation entering said measurement path;

at least one detector sensitive to, and disposed to receive, radiation which has passed through the measurement chamber;

a calibration cell for cooperating with the said path, said cell enclosing a given concentration of the gas whose concentration is to be measured in a sealed enclosure; and a flexible-wall chamber, forming part of said sealed enclosure, for controlling the pressure in the interior of said enclosure in accordance with the ambient temperature and pressure.

2. An analyser according to claim 1, further comprising means for selectively interposing said calibration cell in said measurement path.

3. An analyser according to claim 2, wherein said means for selectively interposing said calibration cell in said measurement path comprise a pivotable arms which supports said cell.

4. An analyser according to claim 1, wherein said calibration cell is closed along the path of the radiation by two windows of material transparent to said radiation.

5. An analyser according to claim 3, wherein said calibration cell is closed along the path of the radiation by two windows of material transparent to said radiation, and said arm carries a compensation window of a transparent material identical to that of the windows of the said cell, and of the same thickness, said compensation window being interposed in the measurement path in the normal operating position of the analyser.

* * * * *